(12) United States Patent
Frieze

(10) Patent No.: US 10,669,513 B2
(45) Date of Patent: Jun. 2, 2020

(54) COMPOSITIONS AND METHODS FOR HANDLING POTENTIAL PRION CONTAMINATION

(71) Applicant: Case Medical, Inc., South Hackensack, NJ (US)

(72) Inventor: Marcia A. Frieze, Alpine, NJ (US)

(73) Assignee: Case Medical, Inc., South Hackensack, NJ (US)

( * ) Notice: Subject to any disclaimer, the term of this patent is extended or adjusted under 35 U.S.C. 154(b) by 0 days.

(21) Appl. No.: 15/720,166

(22) Filed: Sep. 29, 2017

(65) Prior Publication Data

US 2018/0044618 A1    Feb. 15, 2018

Related U.S. Application Data

(63) Continuation of application No. 14/689,113, filed on Apr. 17, 2015, now abandoned.

(60) Provisional application No. 61/987,924, filed on May 2, 2014.

(51) Int. Cl.
| | |
|---|---|
| *C11D 1/72* | (2006.01) |
| *C11D 3/20* | (2006.01) |
| *C11D 3/386* | (2006.01) |
| *A61L 2/18* | (2006.01) |
| *C11D 17/04* | (2006.01) |
| *C11D 1/66* | (2006.01) |
| *C11D 11/00* | (2006.01) |
| *A01N 63/10* | (2020.01) |
| *B08B 3/04* | (2006.01) |

(52) U.S. Cl.
CPC ............ *C11D 17/049* (2013.01); *A01N 63/10* (2020.01); *A61L 2/18* (2013.01); *B08B 3/04* (2013.01); *C11D 1/66* (2013.01); *C11D 1/72* (2013.01); *C11D 3/386* (2013.01); *C11D 3/38618* (2013.01); *C11D 3/38663* (2013.01); *C11D 11/0041* (2013.01)

(58) Field of Classification Search
CPC ....... C11D 1/66; C11D 3/386; C11D 3/38618; C11D 3/48; C11D 11/0023; B08B 3/04; A61L 2/18
USPC ...... 510/238, 383, 393, 421; 134/42; 422/28
See application file for complete search history.

(56) References Cited

U.S. PATENT DOCUMENTS

| | | |
|---|---|---|
| 4,511,400 A | 4/1985 | Faulring |
| 6,613,505 B2 | 9/2003 | Shih |
| 7,303,907 B2 | 8/2007 | Raven |
| 7,393,818 B2 | 7/2008 | McDonnell et al. |

(Continued)

FOREIGN PATENT DOCUMENTS

| | | |
|---|---|---|
| EP | 0141607 B2 | 8/1984 |
| EP | 2206522 A1 | 1/2002 |

(Continued)

OTHER PUBLICATIONS

Australian Patent application Abstract—AU 2002227785 Published 2002, Kritzler et al.
Laino, Enzyme Found to Degrade Prions; Neurology Today Mar. 2004, vol. 4 No. 3, p. 12-15.
Lakshmi, et al; Efficient Degradation of Feather by Keratinase Producing *Bacillus* sp.; International Journal of Microbiology, vol. 2013, Article ID 608321, 7 pages; http://dx.doi.org/10.1155/2013/608321.

(Continued)

*Primary Examiner* — Gregory R Delcotto
(74) *Attorney, Agent, or Firm* — Irving M. Fishman

(57) ABSTRACT

A composition and method of treatment for handling potential prion contamination of surfaces is disclosed. The products include and the treatment uses products that include at least one prion digester enzyme selected from a serine protease in solution with a non-ionic surfactant, a hydrotrope and high purity water

14 Claims, 3 Drawing Sheets

| | Sol 11 | | | | Sol 12 | | | |
|---|---|---|---|---|---|---|---|---|
| pH | X | 8 | 9 | 10 | 11 | 11 10 | 9 | 8 | X |

(56) References Cited

U.S. PATENT DOCUMENTS

| | | |
|---|---|---|
| 7,780,911 B2 | 8/2010 | DiCosimo |
| 8,034,766 B2 | 10/2011 | Croud et al. |
| 8,137,666 B2 | 3/2012 | Chen et al. |
| 8,196,248 B2 | 6/2012 | Kritzler |
| 8,431,526 B2 | 4/2013 | Croud et al. |
| 2002/0192731 A1 | 12/2002 | Shih |
| 2003/0073592 A1 | 4/2003 | McDonnell et al. |
| 2004/0106188 A1 | 6/2004 | Kritzler et al. |
| 2005/0079097 A1 | 4/2005 | Tiarks |
| 2006/0030505 A1 | 2/2006 | Biering et al. |
| 2007/0289614 A1 | 12/2007 | McDonnell |
| 2010/0009884 A1 | 1/2010 | Kritzler |
| 2010/0095988 A1 | 4/2010 | Garet |
| 2010/0240563 A1 | 9/2010 | Jaynes |
| 2010/0260865 A1 | 10/2010 | Kritzler |
| 2011/0086414 A1 | 4/2011 | Kritzler et al. |

FOREIGN PATENT DOCUMENTS

| | | |
|---|---|---|
| GB | 2360041 A | 9/2001 |
| WO | 2002083082 A2 | 10/2002 |
| WO | 2008057293 A2 | 5/2008 |
| WO | 2009052344 A2 | 4/2009 |

OTHER PUBLICATIONS

Okoroma, et al.; (2013) Enzymatic Formulation Capable of Degrading Scrapie Prion under Mild Digestion Conditions.PLoS ONE 8(7):e68099. doi:10.1371/journal.pone.0068099; Jul. 2013, 7 pages.

Sivakumar, et al; Optimization for Keratinase Enzyme Production Using Bacillus thuringiensis TS2; Journal of Plant Sciences 5(3) p. 102-109, (2012).

Chen et al; Characterization and enzymatic degradation of Sup35NM, a yeast prion-like protein; Protein Science (2005), 14:2228-2235. Published by Cold Spring Harbor Laboratory Press.

Booth, et al; Microbial and enzymatic inactivation of prions in soil environments; Soil Biology & Biochemistry 59 (2013) 1-15; http://dx.doi.org/10.1016/j.soilbio.2012.12.016.

Prions Rapidly "Remodel" Good Protein Into Bad, Brown Study Shows; www.brown.edu/Administration/News_Bureau/2005-06 at document 05-019; 2005.

International Search Report from Corresponding PCT/US2015/26401, dated Jul. 22, 2015.

Written Opinion of the International search Authority in corresponding PCT/US2015/26401, dated Jul. 22, 2015.

Czaplicka et al; J. Hazardous Materials, vol. 163, Issues 2-3, Apr. 2009, p. 645-649.

EP 15785461 Supplementary European Search Report dated Jan. 18, 2018, with European Examiner comments (6 pages).

Solution 19

COMPOSITIONS AND METHODS FOR HANDLING POTENTIAL PRION CONTAMINATION

CROSS REFERENCE TO RELATED APPLICATIONS

The present application is a continuation co-pending of U.S. patent application Ser. No. 14/689,113, filed Apr. 17, 2015, now abandoned, which claims the benefit of U.S. Provisional Patent Application Ser. No. 61/987,924, filed May 2, 2014.

FIELD OF THE INVENTION

The present invention is directed to the field of prevention of transmission of prions from a potential source thereof to a different host through an intermediary of a utensil that is used in the preparation of food substances, used in the act of consuming food substances, or a medical device or surgical device used in patients. The present invention is also directed to the field of enzymatic compositions useful as pre-cleaner treatment products, cleaner treatment products, especially those cleaners used to clean protein and protein like materials from various substrates.

BACKGROUND OF THE INVENTION

Enzymatic cleaners combine one or more enzymes with one or more surfactants and other cleaning agents in an effort to clean surfaces and lumens. The enzymes used are typically proteases which degrade proteins by cleaving the amino acid chain so that the post-cleavage fragments can be more easily washed away by the surfactants and water present in the cleaner or in an auxiliary product, typically followed by a rinsing step. Yet, while instrument cleaners containing digestive enzymes (proteases) have proven effective in breaking down organic soils and body fluid, the proteases typically added to surgical instrument cleaners have not been shown to be effective at all in the breakdown of prions, protein like substances causing a variety of wasting diseases, especially under conditions of use recommended for such cleaners. In many instances, cleaners and enzymes that have been potentially discussed for relation to removal and deactivation of prion materials, have been indicated under conditions of use that are environmentally unfriendly or excessively corrosive to the materials being cleaned therewith, require pre-treatment with sterilization, oxidizing agents, peracetic acid or pre-treatment at temperatures above 100° C. prior to treatment with an enzymatic formulation.

Enzymes are catalysts that speed up chemical reactions, and are added to cleaning formulations to speed up the cleaning process. However, enzymes are very specific to the substrates they work on and in the manner in which they work. Proteases break down protein peptide bonds of particular types. Lipases break down fats and/or lipids. Amylases break down carbohydrates and starches. A litany of other enzymes catalyze a host of reactions that are not relevant to the present invention.

A major concern in health care facilities has been the proliferation of hospital acquired infections including surgical site infection when surgical instruments are improperly processed. Europe has been concerned for years about prion diseases Creutzkeldt-Jacob disease in humans (vCJD), and the transmissions of such diseases to humans by consumption of meat from infected animals such as Scrapies in sheep and goats, and bovine spongiform encephalopathy, i.e., mad cow disease. CJD and vCJD has been of a lesser concern in the US and in fact may be under reported. However, Wasting Disease in mule deer and elk has reached epidemic proportions and rapidly proliferated in the United States spreading from animal to animal from contaminated saliva, blood, feces and from vegetation (contaminated primarily due to such agents being deposited on soil absorbed during various plant processes including nitrogen fixation). Health care facilities have used lengthy aggressive parameters to re-process instruments exposed to these prion diseases, or have used incineration, or the costly practice of disposing of single use instruments in connection with many procedures when prion infectivity is suspected.

While the US has had few such cases and has only recently awakened to the risk of prion diseases, that awareness and the need to limit the risk substantially has become more and more visible in recent years.

The Center for Disease Control has stated:

Prion diseases or transmissible spongiform encephalopathies (TSEs) are a family of rare progressive neurodegenerative disorders that affect both humans and animals. They are distinguished by long incubation periods, characteristic spongiform changes associated with neuronal loss, and a failure to induce inflammatory response.

The causative agents of TSEs are believed to be prions. The term "prions" refers to abnormal, pathogenic agents that are transmissible and are able to induce abnormal folding of specific normal cellular proteins called prion proteins that are found most abundantly in the brain. The functions of these normal prion proteins are still not completely understood. The abnormal folding of the prion proteins leads to brain damage and the characteristic signs and symptoms of the disease. Prion diseases are usually rapidly progressive and always fatal.

Prions can be transmitted by ingestion of meat infected with prions, and lead to brain wasting diseases. Of greater concern however, has been the actual and potential for transfer of such infectious agents from patient to patient in hospital settings from blood transfusions and from surgical instruments, especially from dirty surgical instruments (and even from apparently cleaned instruments having residual prion contamination), most especially from those instruments used in brain and neurological procedures, and even from instruments used in eye, spleen, appendix, and tonsil surgeries.

While cleaning is the critical first step in the decontamination of surgical instrumentation, the removal of prions by traditional means, enzymatic solutions such as those with protease enzymes, high level disinfection and sterilization even when preceded by high alkaline detergents has not been shown to effectively destroy or remove prions from medical devices. (Furthermore, use of highly acidic (pH 4 and below) or highly alkaline (pH 11 or above) compositions are detrimental to the instrument surfaces needing to be cleaned and therefore cleaners using such pH extreme formulations are only minimally economically more advantageous than using disposable equipment). Prions are believed to cause not only known diseases such as CJD, vCJD, Scrapies and other wasting diseases, but also may have a direct link to other neurological diseases such as Alzheimer's, dementia, Parkinsons Disease, MS and other neurological diseases.

By simply removing prions and rendering them ineffective by specific enzymes in a surfactant blend that is water soluble, free rinsing, biodegradable and environmentally preferred, the simple act of pre-cleaning, cleaning, and rinsing such devices from soiled instruments and equipment can become a major life saving initiative and curb a potential epidemic. While most surgical devices must be incinerated after exposure to prions or, in some facilities, using single use instruments at a huge expense in such cases, most cases of prion disease and transmission are unknown and under reported. The consequences to public health can be catastrophic and the cost to the public health system enormous when such an event occurs and frightening when under reported.

Multi-enzymatic cleaners for medical instruments preparatory to sterilization of such instruments in existing sterilizers generally do not have enzymes that are suitable for attacking prion materials and therefore rely on the "mechanical action" or sonication of the cleaning process to hopefully remove such prion contaminants. While such action can remove a wide range of contaminant materials and soils, not all surfaces can be effectively cleaned by such mechanical action and even where generally effective results can so be obtained, there is still a significant chance of residual contamination. With respect to prion materials, even minute residual contamination is of concern since prion materials can very rapidly convert normally folded materials into improperly folded analogs in an iterative process so that even such small residual contamination can be highly problematic. In 2005, in an article published at http://www-.brown.edu/Administration/News_Bureau/2005-06-05-109.html. entitled "Prions Rapidly "Remodel" Good Protein Into Bad, Brown Study Shows", it was reported by Serio et al, in an article published in Nature, that prions convert healthy protein into abnormal protein through an ultrafast process similar to DNA replication. Thus, prion contamination has become a growing concern in the medical field. Other compositions require conditions of use to obtain prion disinfection with extreme pHs (generally under pH 4 or over pH 11) making them unsuitable for use with the substrate being cleaned. Other methods require long exposure times from at least one hour to 48 hours to an enzymatic formulation or require multiple steps which may still be ineffective and have the potential to delay surgical procedures and affect patient care.

Similar concerns of contamination with prions have been raised in connection with meat processing plants due to the possibility of an infected animal not presenting with symptoms before slaughter not being detected.

OBJECTS OF THE INVENTION

It is an object of the invention to provide a method of utilizing an enzymatic cleaner capable of effectively digesting prion proteins under about neutral to mild to mid-alkaline conditions, preferably about pH 7 to about pH 10.

It is another object of the invention to provide a method of using an enzymatic cleaner for utensils and/or medical instruments at neutral to mild to mid alkalinity conditions using a composition having multiple enzymes so as to have a broad spectrum of protein cleaning activity, wherein at least one of the enzymes in the multi-enzymatic cleaner is capable of digesting prions under about mild to mid-alkaline conditions, preferably about pH 7.5 to about pH 10.

It is still a further object of the invention to provide a method of cleaning medical instruments wherein the cleaner contains at least one enzyme capable of digesting prions under about mild pH conditions, preferably at pHs of about 8 to about 9.

Yet another object of the invention is to provide a method of cleaning instruments and utensils utilized in the meat processing industry so as to decontaminate surfaces that may have been exposed to a prion contaminated meat.

Still another object of the invention is to provide a stable formulation of a cleaner containing an enzyme capable of digesting a prion under about neutral to about mildly alkaline to mid alkaline pH conditions under conditions currently in place in re-processing departments of health care facilities.

Another object of the invention is to provide a stable formulation of an enzymatic cleaner formulation containing at least one enzyme capable of digesting a prion under about mildly alkaline pH conditions.

Still another object of the invention is to provide a pre-cleaner treatment product for digesting prions prior to use of a cleaner product.

Still another object of the invention is to provide a method of using certain marketed formulations of cleaners under particular conditions of use so as to achieve prion cleaning.

Yet another object of the invention is to provide a modified version of existing cleaners for use under particular conditions of use so as to achieve prion cleaning.

Yet another object of the invention is to provide a modified version of existing cleaners for use under particular conditions of use so as to achieve prion inactivation and degradation.

Yet another object of the invention is to provide a product for treatment of surfaces (which animals or humans that may have infectious prions come in contact), as a means of inhibiting transmission of prions from such contaminated hosts to other uncontaminated hosts.

Still a further object of the invention is to provide an impregnated wipe having at least one enzyme capable of digesting a prion impregnated in the wipe.

Yet a further object of the invention is to provide a gel, foam, or spray composition having at least one enzyme capable of digesting a prion Still yet another object of the invention is to provide a method of making the formulations referred to above.

Even further objects of the invention will be apparent to those of ordinary skill in the art after having read the present specification and claims.

BRIEF DESCRIPTION OF THE INVENTION

The foregoing objects of the invention and others can be realized by the formulations detailed below and in use of other available formulations modified either in their compositions or in their manner of use as appropriate. The present invention is directed to at least the following embodiments:

(a) an enzymatic formulation containing at least one enzyme which is capable of breaking down prions into fragments (or degrading prions into entities) that are not infectious as prions, the enzyme in combination with at least one non-ionic surfactant;

(b) use of such a formulation in a cleaning process of surfaces or instruments that are potentially closed to infectious prion materials.

(b) use of such a formulation as pre-treatments in a cleaning process of surfaces with cleaning of instruments that are potentially exposed to infectious prion materials.

The formulations of the invention can be (a) simply these enzymes in combination with non-ionic surfactants and (optionally certain anionic surfactants) in a suitable carrier optionally with auxiliary formulation agents or (b) may be more complex formulations containing additional cleaning agents. The formulations can be used as pre-treatments to other cleaning operations, and those with additional cleaner components can be used as stand-alone cleaner products in cleaning operations as well. The formulations can be in the form of solutions, suspensions, solid, semisolid formulations, gels, foams or impregnated wipes. They may be in ready to use form or in concentrates that are diluted for use. The products of the invention can be used to clean a wide variety of surfaces and lumens that are suspected of being exposed to prions and potentially other infectious agents.

BRIEF DESCRIPTION OF THE DRAWINGS

The Figures are the respective immunoblots for the correspondingly labeled test solutions mentioned in the tables in Example 3.

DETAILED DESCRIPTION OF THE INVENTION

Figure 1:
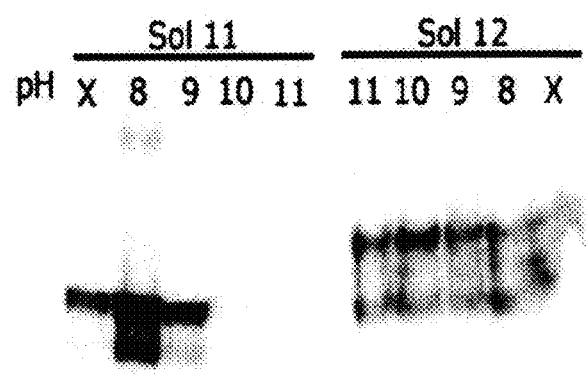
FIG. 1 is the immunoblots resulting from test solutions 11 and 12.
Figure 2:
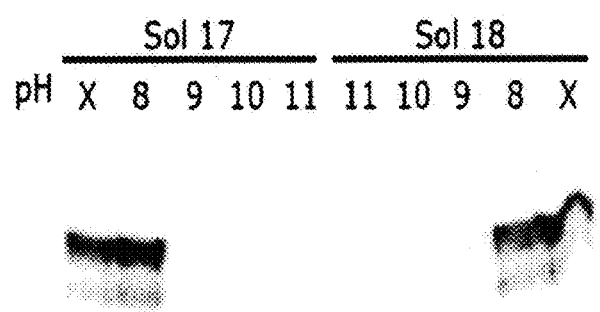
FIG. 2 is the immunoblots resulting from test solutions 17 and 18.
Figure 3:
FIG. 3 is the immunoblots resulting from test solution 19, under shaking conditions and under ultrasonic condition.
Figure 4:
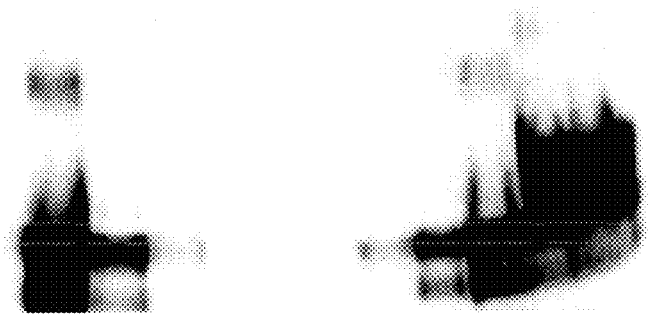
FIG. 4 is the immunoblots resulting from test solutions 5A and 9.
Figure 5:
FIG. 5 is the immunoblots resulting from test solutions 8 and 10.
Figure 6:
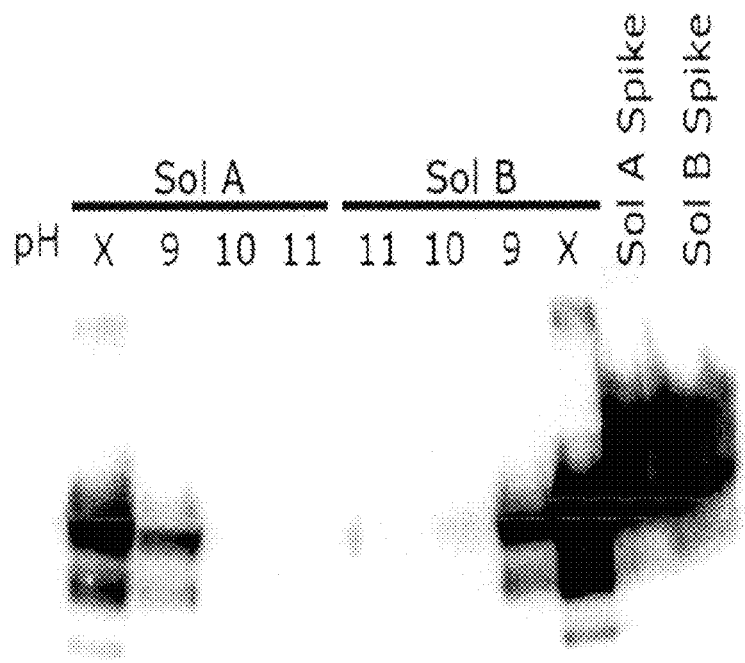
FIG. 6 is the immunoblots resulting from test solutions A and B.

The present invention, in its simplest embodiment is a simple solution or suspension of at least one of the enzymes selected from prion degrading serine proteases (inclusive of, without limitation, Alcalase, Savinase, keratinases, nattokinase, Proteinase K, and mixtures thereof) in conjunction with non-ionic surfactants (such surfactants being detailed more fully below). Such solutions or suspensions are prepared by placing the respective enzyme into a suitable carrier, preferably an aqueous carrier which may or may not contain other ingredients, along with the non-ionic surfactant. The aqueous carrier is generally water, which may be high purity water (such as, without limitation, distilled water, deionized water or reverse osmosis water), preferably a high purity water such as distilled water or reverse osmosis water. It should be noted that it was surprisingly found that use of high purity water as the carrier (with or without additional components as set forth more specifically below) and as dilution media, when the formulation was diluted one was satisfactorily able to operate at a pH below the optimal pH of the particular enzyme with respect to prion attack and still achieve the desired results. In contrast, when ordinary tap water is used to dilute the concentrated clearer, a number of enzymes were found to be active against prions only at extreme pH (i.e., at 10 or beyond, especially at pH 11 and beyond). Such simple embodiments can be used as a pre-cleaner/disinfectant product for treating surfaces in advance of subsequent cleaning steps. It is recognized that there may be some existing products that fall within this generalized description and it is the inventors intention that existing formulations that are prior art hereto are excluded from being within the claimed formulation invention. To that end, following the examples is descriptive material to more explicitly disclaim such prior art formulations from the scope of the claimed formulations. However, it should be noted that in many instances the claimed formulations are not recommended for use under the same conditions of use as described herein. Hence, these potentially excluded formulations are suitable for use in the methods of the present invention under the conditions of use set forth herein in treating prion infected substrates, in disinfecting substrates from prion materials, and in digesting or destroying such prion materials. In the event that a prior art formulation is found to be used under the conditions of use described more fully below, that particular formulation under those particular conditions of use is also to be recognized as not within the scope of the present invention.

In its more complex forms, the invention products include at least prion digesting enzyme selected from serine proteases (including, but not limited to alcalase, savinase, Proteinase K, keratinase, nattokinase and mixtures thereof), along with components selected from (a) at least one other enzyme typically found in enzymatic cleaners for removal of soils and is active at the operating pH of the entire formulation (including, without limitation, amylase, lipase, cellulase, endo and exo glucanases, and mixtures thereof);

(b) at least one surfactant selected from non-ionic surfactants (including, without limitation, polyethoxylated alcohols such as $C_{6-12}$ (branched or unbranched)alkyl-$(OCH_2CH_2)_{3-6}OH$, especially useful are the narrow range varieties such as those having a $C_8$ branched alcohol ethoxylated with about 4 moles of ethylene oxide), most preferably 2-ethylhexyl-$(OCH_2CH_2)_4OH$;

(c) at least one hydrotrope selected from anionic surfactants such as, without limitation, (i) alkali metal salts of sulfated (unsubstituted or mono or di $C_{1-2}$alkyl substituted) $C_{6-10}$ aryls, particularly, (i) sodium or potassium salts of (unsubstituted or mono or di-$C_{1-3}$alkyl substituted phenylsulfonate, preferably sodium xylenesulfonate (aka SXS), sodium toluene sulfonate (aka STS) or sodium cumenesulfonate (SCS), or (iii) alkyldiphenyloxidedisulonate alkali metal salts, such as without limitation those in the Dowfax family;

(d) optionally propylene glycol, (e) optionally calcium chloride, (f) water (preferably a high purity water).

(g) optionally preservative;

(h) optionally buffer suitable to buffer to the appropriate pH preferably selected from (without limitation to) TRIS (aka trihdroxymethyl-methylamine) especially for buffering in the pH range of about 8 to about 9, bicarbonate buffer especially for buffering in the pH range of about 10 to about 11, or Bicine (aka N,N-bis(2-hydroxyethyl) glycine having a pKa of 8.5 at 20° C.); and mixtures thereof along with any needed pH adjuster, the pH adjuster including, but not limited to alkali metal (especially sodium or potassium) hydroxide; and (i) optionally an anti-corrosion agent (especially needed when the formulation pH is in excess of pH of about 9) (aka corrosion inhibitor).

The formulation pH is selected from a pH within the range of about 7 to about 11, preferably about 7.8 to about 10, more preferably about pH 8 to about pH 9. Depending on the particular enzyme mix desired, the pH is selected from those of about pH 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, and about 11.0. Furthermore, notwithstanding the particular pH ranges mentioned above, each of the pHs recited in the immediately preceding sentence may serve as a lower limit or as an upper limit of a new range constructed therefrom. Furthermore, for purposes of the pH range, the term "about" should be construed as +/−0.05 pH units. Still further, for each pH point designated above as "about" a particular pH, that particular pH without the designation of "about" is deemed to be expressly disclosed herein.

While any protease that can degrade prions can be used in the present invention, the proteases used are preferably selected from serine proteases (including, but not limited to, alcalase, savinase, proteinase K, nattokinase and keritinase and mixtures thereof). For the keratinase, it is preferable to use a keratinase selected from the group consisting of *Bacillus licheniformis* N22 keratinase; and the keratinases produced by *Bacilius subtilisis; Bacillus cereus* and *Bacillus pseudofirmus*. (See Academic Journal of Plant Sciences 5(3); 102-109, 2012), with *Bacillus licheniformis* N22 keratinase being most preferred. This particular enzyme was described as being capable of degrading Scrapie Prion under mild digestion conditions, by Okoroma et al, *Enzymatic Formulation Capable of Degrading Scrapie Under Mild Digestion Conditions*; PLOS One, July 2013, Vol; 8, Issue 7, pg 1-7, e68099. Nattokinase is an extracellular enzyme secreted by *B. subtilis natto* and belongs to the serine protease family. Because nattokinase is an edible enzyme and has been used as a nutrient supplement, it can be used to digest amyloids in the body. Moreover, prions are infectious agents which lead to various prion diseases. The disease can be transmitted through diet, surgery, and perhaps blood transfusion. Nattokinase can be used to remove infectious prions from animal feed, surgical instruments, and blood products. Savinase is available from multiple sources, specifically Novozyme and has an active range from pH 7 to 11. Alcalase is commercially from multiple sources, specifically Novozyme, and has an active pH range of 7-10. Proteinase K, while commercially available, is currently very expensive and therefore not generally commercially viable for use in the present invention. However, it is a suitable enzyme for use in the present invention and will be of considerable benefit if and when the economies of scale bring the price to more reasonable levels.

Optional additional enzymes can be present in the simple pre-cleaning treatment composition. These are selected from various additional proteases (those not of the 5 listed in the preceding paragraph), and include, without limitation, lipases, cellulases, carbohydrases and amylases. When present, these optional enzymes are present in amounts which act significantly on breaking down non-prion proteins, fats, and starches and other carbohydrates. Thus, certain preferred embodiments of the compositions of the invention therefore also include those having:

(a) at least one prion-degrading enzyme; and
(b) one or more of (i) one or more enzyme which does not degrade prions significantly, (ii) one or more lipases, (iii) one or more carbohydrases (such as, without limitation, celluloses) and/or (iv) one or more amylases;
(c) one or more non-ionic surfactants as mentioned above and
(d) at least one carrier material selected from high purity waters, and
(e) may optionally further contain a suitable hydrotrope (selected from anionic surfactants mentioned above) for maintaining the various components in a solution or suspension;
(f) optionally propylene glycol;
(g) optionally calcium chloride;
(h) optionally one or more preservatives;
(i) optionally one or more buffers and auxiliary pH adjusters.

Such formulations having at least one prion degrading enzyme and at least one enzyme which is not a prion degrader but is selected from, lipases, carbohydrases, cellulases and amylases, and at least one carrier also preferred embodiments, and can also be used as a pre-treatment to a cleaning regimen optionally using other cleaning agents.

The lipases can be, without limitation, Lipex (available from Novozyme).

The carbohydrase is, without limitation, preferable selected from one or more cellulases. The cellulases are, without limitation, preferably selected from, without limitation, CSOE342 f Celluclean from Novozyme The amylases for use in the present invention include, but are not limited to, alpha amylases, more preferably Termamyl from Novozyme.

Each of the foregoing products of the invention contains at least one non-ionic surfactant; as set forth above and optionally contains an anionic surfactant (as a hydrotrope) as set forth above. Preferably both a non-ionic surfactant and an anionic surfactant are present. In some embodiments, concentrates of the prion degrading enzymes can be added to pre-existing cleaners (whether or not such pre-existing cleaners contain enzymes that do not degrade prion, but are selected from proteases, lipases, carbohydrases and/or amylases or mixtures thereof). Non-limiting pre-existing cleaners or current concentrated enzymatic solutions, to which the prion degrading enzyme(s) can be added include, without limitation products sold by Case Medical Inc (such as without limitation, Case Solutions, SuperNova Multi-Enzyme Cleaner (CSNC25, CSNC01), Pentaprep (CSA011), Pentazyme, BioGone, NOVAPLUS and NOVAPLUS EXPRESS Multi-enzymatic cleaners and PentaWipes); and without limitation products sold by other companies, such as without limitation, Cidex (sold by J&J), Empower (sold by Metrex), Prolystica and Klenzyme (sold by Steris), Ruhof, Gentinge, EcoLab, Certol and other products and suppliers of instrument chemistries.

Importantly, the existing products, Case Solutions, NOVAPLUS and SuperNova multi-enzymatic cleaners, under conditions of 10 to 30 minute exposure, elevated concentration up to 10× to 12× the recommended general cleaning dilution rate (10 fold to 12 fold more total solid after dilution than pre-existing recommendations), and pH adjustment to a higher pH (mild to mid-alkalinity) (i.e., higher than currently recommended for general cleaning) degraded prion infected brain tissue ≥700 fold (beyond the detection limit of the immunoblot used to assess prion degradation).

In the alternative, the compositions of the present invention (which are simultaneously prion digesters and cleaner products) can be prepared by combining the respective enzymes that are prion digesters with the other enzymes that are optionally present along with the surfactants and auxiliary agents that are in cleaners more generally. The formulations can be prepared in analogous fashion to those enzymatic cleaners having enzymes that are not prion digestors (as defined in the present invention) by including the prion digestors in the same fashion and in the same general order as the non-prion digester enzymes are included in the other cleaner products. If, in doing so, the pH of the composition is outside of the ranges set forth hereby, either an acid, or base (inorganic or organic) can be used to adjust the pH into a range as stated herein. While the pH can be adjusted after the prion digester enzyme is added, it is preferable to adjust the pH into a suitable range before adding the prion digestor.

In the instant description of the invention, concentrations are being described (unless explicitly stated otherwise) with respect to a "concentrate" which is intended to be diluted for actual use in a ratio of 1 part by volume to 128 parts by volume of water in actual disinfection use. More concentrated formulations having a corresponding higher dilution factor and more dilute formulations having a lesser dilation factor (inclusive of ready to use formulations which have no dilution) that result in the same formation for use as the described concentrates when diluted as indicated are fully within the present invention. Furthermore, % are described as % by weight based on the full formulations of the concentrates. Still further, wherever % by weight is described, the corresponding formulation using parts by weight by simply replacing "% by weight" with "parts by weight" is intended as being specifically disclosed herein. Each of the prion digester enzymes are present generally in an amount that is 0.01% to 15% (by weight) of the composition as finally formulated; preferably 0.025% to 12.5%, more preferably 0.05% to 10%, still more preferably 0.075% to 7.5%, more preferably 0.1% to 5%, still more preferably 0.1% to 1%, with alternate ranges selected from those having a minimum selected from 0.01%, 0.025%, 0.05%, 0.06%, 0.07%, 0.08%, 0.09%, 0.1%, 0.2%, 0.3%, 0.4%, 0.5%, 0.6%, 0.7%, 0.8%, 9%, 1.0%, 1.25%, 1.5%, 1.75%, 2.0%, 2.5%, 5.0%, 7.5%, and 10% and an upper range limit (which is higher than the lower limit selected) selected from 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.55, 3.0%, 3.5%, 4.0%, 4.5%, 5%, 6%, 7%, 8%, 9%, 10%, 11%, 12%, 13%, 14%, and 15%. These amounts can be selected as either independent amounts of each of the prion digesting enzymes or as cumulative amounts of all prion digesting enzymes in the composition. The non-prion digestor proteases when present can be present independently in an amount that is 0.01% to 15% (by weight) of the composition as finally formulated, preferably 0.25% to 1.25%, more preferably 0.05% to 10%, still more preferably 0.075% to 7.5%, more preferably 0.1% to 5%, still more preferably 0.1% to 1%, with alternate ranges selected from those having a minimum selected from 0.01 %, 0.025%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.5%, 1.75%, 2.0%, 2.5%, 5.0%, 7.5%, and 10% and an upper range limit (which is higher than the lower limit selected) selected from 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.55, 3.0%, 3.5%, 4.0%, 4.5%, 5%, 6%, 7%, 8%, 9%, 10%, 11%, 12%, 13%, 14%, and 15%. When present, the other enzymes, such as without limitation, amylases, lipases, carbohydrases, etc., can each be present independently in an amount that is 0.01% to 15% (by weight) of the composition as finally formulated; preferably 0.025% to 12.5%, more preferably 0.05% to 10%, still more preferably 0.075% to 7.5%, more preferably 0.1% to 5%, still more preferably 0.1% to 1%, with alternate ranges selected from those having a minimum selected from 0.01%, 0.025%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.5%, 1.75%, 2.0%, 2.5%, 5.0%, 7.5%, and 10% and an upper range limit (which is higher than the lower limit selected) selected from 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.55, 3.0%, 3.5%, 4.0%, 4.5%, 5%, 6%, 7%, 8%, 9%, 10%, 11%, 12%, 13%, 14%, and 15%. More concentrated (up to the limit of solubility) or less concentrated (down to the in-use diluted concentration of a ready-to-use product) can also be used provided all of the components (other than water) are proportional to each other in the same proportions as set forth herein without consideration of such more concentrated or more dilute solutions complete invention solutions (i.e., a solution having all of the mandatory components of at least one invention solution).

The non-ionic surfactants can independently be present in amounts of ranges having a lower value and upper value selected from the following values (provided the lower end of the range is in fact a lower value than the upper end of the range created): about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, and about 15% up to a total non-ionic surfactant content of: about 15%. As mentioned above, more concentrated (up to the limit of solubility) and more dilute (down to the diluted ready-to-use concentration) are also suitable provided that all components (other than the water content) that are present are in proportion to each other as a formulation that is otherwise within the present invention without consideration of more dilute and more concentrated variations thereof.

Each of the anionic surfactant/hydrotropes can independently be present in amounts of ranges having a lower value and upper value selected from the following values (provided the lower end of the range is in fact a lower value than the upper end of the range created): about 1%, about 1.5%, about 2%, about 2.5%, about 3%, about 3.5%., about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, and about 15%, up to a total anionic surfactant content of about 15%. As mentioned above, more concentrated (up to the limit of solubility) and more dilute (down to the diluted ready-to-use concentration) are also suitable provided that all components (other than the water content) that are present are in proportion to each other as in at least one formulation that is otherwise within the present invention without consideration of more dilute and more concentrated variations thereof.

The propylene glycol component, when present, can independently be present in amounts of ranges having a lower value and upper value selected from the following values (provided the lower end of the range is in fact a lower value than the upper end of the range created): about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, about 20%. As mentioned above, more concentrated (up to the limit of solubility) and more dilute (down to the diluted ready-to-use concentration) are also suitable provided that all components (other than the water content) that are present are in proportion to each other as in at least one formulation that is otherwise within the present invention without consideration of more dilute and more concentrated variations thereof.

The buffer, when present, can be present in amounts of up to a total amount selected from about 5%, about 4.5%, about 4%, about 3.5%, about 3%, about 2.5%, about 2%, about 1.5%, about 1.25%, about 1.1%, about 1%, about 0.9%, about 0.75%, and about 0.5% of the formulation. As mentioned above, more concentrated (up to the limit of solubility) and more dilute (down to the diluted ready-to-use concentration) are also suitable provided that all components (other than the water content) that are present are in proportion to each other as in at least one formulation that is otherwise within the present invention without consideration of more dilute and more concentrated variations thereof.

The preservative, can be any suitable preservative typically used in enzymatic compositions, and preferably includes, without limitation, those selected from the group isothiazolinones (particularly, without limitation, methylisothiazolinone, benzisothiazolinone and mixtures thereof, such as without limitation, the commercially available Microcare SI), isothiazolones, bronopol, aldehydes, and mixtures thereof. When present, the preservative is typically used in amounts of ranges having a lower value and upper value selected from the following values (provided the lower end of the range is in fact a lower value than the upper end of the range created): about 0.05%, about 0.010%, about 0.015%, about 0.020%, about 0.025%, about 0.0255%, about 0.026%, about 0.030%, about 0.035%, about 0.040%, about 0.045%, and about 0.05% of the formulation. As mentioned above, more concentrated (up to the limit of solubility) and more dilute (down to the diluted ready-to-use concentration) are also suitable provided that all components (other than the water content) that are present are in proportion to each other as in at least one formulation that is otherwise within the present invention without consideration of more dilute and more concentrated variations thereof.

For formulations that are less than pH 9, a corrosion inhibitor is not required, but may still be included. When the pH is at or above 9, a corrosion inhibitor is usually present and when at or above pH 10, it is always present. The corrosion inhibitors for use in the present invention include, without limitation, 1-ethyl-3-methylimidaolium dicyanamide (aka EMID) and other environmentally friendly or environmentally preferred corrosion inhibitors, such as, without limitation fatty amide corrosion inhibitors, pyridine corrosion inhibitors, imidazoline corrosion inhibitors, azole corrosion inhibitors, all of which are generally known to those of ordinary skill in the art, and mixtures thereof. When the substrate is a passivated stainless steel or an anodized aluminum, there is a lesser need for a corrosion inhibitor and therefore when using the invention formulations at the higher pHs for such substrates, the corrosion inhibitor may be eliminated. Notwithstanding the above, where desired, less environmentally friendly corrosion inhibitors, most of which are toxic compounds, may be used, but are generally less desirable due to their toxicity and/or being environmentally unfriendly. When present, the corrosion inhibitor can be present in amounts of selected from ranges having a lower value and upper value selected from the following values (provided the lower end of the range is in fact a lower value than the upper end of the range created): about 0.025%, about 0.05%, about 0.075%, about 0.1%, about 0.125%, about 0.15%, about 0.175%, about 0.2%, about 0.225%, about 0.25%, about 0.25%, about 0.275%, 0.3%, 0.335%, about 0.35%, about 0.375%, about 0.4%, about 0.425%, about 0.45%, about 0.475%, and about 0.5% of the formulation. As mentioned above, more concentrated (up to the limit of solubility) and more dilute (down to the diluted ready-to-use concentration) are also suitable provided that all components (other than the water content) that are present are in proportion to each other as in at least one formulation that is otherwise within the present invention without consideration of more dilute and more concentrated variations thereof.

The formulations of the present invention can be assembled in any order that is convenient and desirable under the circumstances. These will be understood and appreciated by those of ordinary still in the art stated. As stated, in some cases the prion digesters for use in the present invention, once selected may be added to an otherwise pre-formed product containing simply carrier substances or containing other enzymes that do not qualify as prion digesters or containing non-enzyme cleaning agents or formulation auxiliary agents that are useful for purposes of formulation stability, preservation, or maintaining compatibility between the other components of the formulation.

The formulations of the invention can be in the form of (without limitation) solutions, suspensions, lotions, solid or semisolid formulations (such as creams, gels, thickened emulsions), etc., although solutions are generally preferred. The invention formulations can be used in the form of (without limitation) a spray, a liquid applied to a substrate directly via an applicator material such as (without limitation) a sponge, a cloth, etc; or may be impregnated into an application cloth or "towelette".

The formulations of the invention are preferably used as solutions in which the substrate to be treated is immersed with or without agitation, with or without sonication. Sonication and agitation are independently preferably applied. Sonication is most preferably applied, and when used, allows for reductions in one or more of contact time, temperature, and solution concentration toward the lower end of the ranges identified herein than when sonication is not used. The substrate is preferably submerged in the invention formulation which is maintained at temperatures in the range of about 50° C. to about 65° C., preferably about 55° C. to about 60° C., more preferably at about a temperature selected from 55° C., about 56° C., about 57° C. about 58° C., about 59° C. and about 60° C. (with each specific temperature point, without the qualifier "about" being intended as being disclosed specifically herein as well). Contact time between the alleged contaminant to be treated and the invention formulation should be from at least about 10 minutes to about 30 minutes or longer, although longer times do not provide additional appreciable benefit, there is no problem with utilizing longer contact times, and as such, the use of longer contact times is deemed to be within the scope of the invention, unless specifically disclaimed. Other preferable contact times include about 11 minutes, about 11.5 minutes, about 12 minutes 12.5 minutes, about 13 minutes, about 13.5 minutes, about 14 minutes, about 14.5 minutes, about 15 minutes, about 15.5 minutes, about 16 minutes, about 16.5 minutes, about 17 minutes, about 17.5 minutes, about 18 minutes, about 18.5 minutes, about 19 minutes, about 19.5 minutes, about 20 minutes, about 20.5 minutes, 21 minutes, about 21.5 minutes, about 22 minutes, about 22.5 minutes, about 23 minutes, about 23.5 minutes, 24 minutes, about 24.5 minutes, about 25 minutes, about 25.5 minutes, about 26 minutes, about 26.5 minutes, about 27 minutes, about 27.5 minutes, 28 minutes, about 28.5 minutes, about 29 minutes, about 29.5 minutes, and about 30 minutes, specifically as well as ranges selecting a lower end of the range from the foregoing list and an upper end of the range also selected from the foregoing list, provided that the upper end of the range is greater than the lower end of the range. It will be noted that lower temperatures (within the above stated ranges) may require longer contact times, but the precise combination between a particular temperature and contact time can readily be arrived at by those of ordinary skill in the art. Pre-cooking (i.e., using temperatures in excess of 75° C.) of the contaminated substrate to be treated is not required and in preferred embodiments is specifically excluded from the methods of use. In other embodiments, where desired, such pre-cooking may be desired and the addition of a pre-cooking step is not excluded, particularly when such steps are used in combination with novel invention formulations. Still preferred methods of use exclude such pre-cooking steps.

An additional embodiment of the invention includes, without limitation, a wipe impregnated with an invention formulation, as well as a spray, a foam or a gel formulation, which can be used for direct application to a substrate to be treated, and especially as a pre-treatment application. The wipe serves two functions to provide friction or wiping which removes organic soil or bioburden during cleaning. The impregnated wipe also can serve as a cover when placed over the used devices to contain the contaminated materials on device surfaces while keeping devices moist and providing breakdown of bioburden and organic soil thus facilitating the cleaning process.

The enzymatic cleaning product can be sprayed onto the surfaces of used devices as a pre-treatment foam applicator or gel to be treated and mechanically scrubbed by hand or with mechanical scrubbers of any convenient type. It is known that prions adhere to metal surfaces and in addition to chemically breaking down prions into fragments that are not infectious, it is important to break the bonds that adhere the prion materials to the metal substrates. Thus, it is important to either scrub the surfaces or have additional cleaner components that are soluble in aqueous media present, most preferably utilizing both scrubbing and chemical cleaning components in concert.

Where desired, the additional chemical components can be in the same composition with the prion digesters or as separate compositions for use in a follow on cleaning operation. The important aspect is that during the complete cleaning of the surface being treated, there is either concurrent or sequential enzymatic prion degradation, mechanical scrubbing (either by hand or by mechanized scrubbers) and non-enzymatic chemical cleaning in order to best assure deactivation of the prion material and its removal. Preferably, in the method of the invention, the product having prion deactivation activity is applied as a "soak" in which the substrate to be cleaned is immersed in the product in question at an appropriate dilution (if needed) and temperature, so that sonication or mechanical cleaning can follow. The substrate is allowed to remain submerged in the solution for the above mentioned contact time. Mechanical scrubbing can be applied at this time, although it is preferable to use sonication so as to more effectively address contamination that might be present in small spaces specially around joints, or within small lumens and other interior spaces that are difficult to reach by manual scrubbers. Once the formulations described above have been in contact with the surfaces to be treated for the prescribed period, and scrubbing has been done, and the surfaces rinsed, the so treated surfaces can be, where desired, and preferably are, subjected to additional disinfection methods such as autoclaving, steam sterilization, and/or gas plasma sterilization among others known in the distinction and sterilization arts.

In the foregoing, where not specifically addressed above, when the term "about" precedes a definite number that is not a range endpoint, it is intended to convey +/−10% of that number. When the term "about" precedes a range endpoint, it is intended to convey either +/−10% of the number it precedes or the term "about" is applied to the larger endpoint and then that same absolute amount is applied to the lower endpoint. By way of example, in the range of "about 2 minutes to about 6 minutes" one shall interpret the range to be either "108-132 seconds" (120+/−10% of 120) to "324-396 seconds" (360+/−10% of 360) or, if not invalidating, the range of 120 seconds (+/−36) to 360 seconds (+/−36). In addition, in the latter case, the application of the larger end absolute +/− amount to the lower end of the range shall be deemed to not include such amounts as to reduce the lower end of the range to zero (for example, a "30 second" endpoint +/−36 seconds would be construed as a positive value not including zero up to 66 seconds"). In any case where the term about is used, the actual value of the term without the "about" shall be deemed disclosed as well. In any event, the interpretation in this paragraph shall not apply to prior paragraphs where the term "about" was specifically defined with respect to the term of concern in such earlier paragraph.

Having described the present invention in the above disclosure, the following Examples are presented by way of exemplification and do not limit the scope of the invention.

EXAMPLE

Example 1—

One preferred formulation of the present invention is prepared according to the formulation below.

| Component | Percent by wt |
|---|---|
| Water | 57.12 |
| Calcium Chloride | 0.3 |
| Propylene Glycol | 10 |
| EthylHexyloxytetraethoxylate (Non-ionic surfactant) | 10 |
| Sodium Xylene Sulfonate (Hydrotrope) | 8.8 |
| Lipase | 3.5 |
| Amylase | 2.5 |
| Alcalase | 4.75 |
| Celluclean | 3 |
| Microcare ® SI | 0.03% |

To 100 ml of the above formulation is added 0.1 g of bicine which gives a pH of 6.54. The formulation is then adjusted to pH 9 using approximately 1 ml of potassium hydroxide.

The above, pH adjusted formulation is used as a soak for disinfecting prion contaminated substrates by dilution at the rate of 1 fl oz per gal of soak solution (i.e., a 1:128 ratio) when the dilution media is a high purity water and 1.5 fl oz per gallon (i.e., a 1:about 86 ratio) when the dilution media is a tap water.

Example 2

Parallel formulations to those in Example 1 feeing more concentrated or less concentrated by varying the percentage of water above only are prepared and may be used in appropriate dilutions to achieve the same concentrations in actual use in a soak solution as the soak solution in Example 1. A few non-limiting examples are set forth in the table below, which after pH adjustment in a proportional amount with the biocine and KOH are utilized in the approximate indicated dilution rate to achieve essentially the same soak solution as in Example 1.

| Variation form Example 1 | Water | Solids | Dilution rate with high purity water to achieve same soak solution as in Example 1 |
|---|---|---|---|
| ½ strength | 78.575 | 21.425 | 3 fl oz/gal (1:43) |
| ⅔ strength | 71.44 | 28.56 | 2 fl oz/gal (1:64) |
| Ready to use | 99.665 | 0.335 | No dilution |

Example 3

A standard formulation for comparative testing is prepared containing high purity water, calcium chloride as a firming agent, propylene glycol, a tetraethoxylate of an octanol as a non-ionic surfactant, sodium salt of a sulfated aryl as a hydrotrope, and a preservative. To this basic set of ingredients, the specific enzymes are added as indicated in the table below and a buffer is added as indicated in the table below. Test samples are prepared using hamster brain homogenate infected with transmissible mink encephalopathy. After test samples are prepared, they are exposed to the various solutions indicated in the table below by adding a sufficient amount of the indicated solution to result in a dilution of 1:51.2 by volume using high purity water (resulting in analogous diluted solutions similar to that of Example 1 diluted at the ratio of 1:128). To this diluted formulation is added 0.6% (by volume) of the brain homogenate which was 3 mg of prion infected brain homogenate to 500 μL of diluted solution. Exposure time, temperature and concentration of enzymes are varied as indicated. pH is varied for each condition set in the range of neutral to pH 11. After the appropriate exposure time, immunoblots are prepared to assess remaining protein. The immunoblots are shown in the Figures and identified with the solution labels as treated in the following table.

|  | #11 | #12 | #13 | 17 | 18 | 19 (shake) | 19 (sonicate) |
|---|---|---|---|---|---|---|---|
| Savinase | X | X | X | X | X | X | X |
| Alcalase | 4% | X | X | 1.9% | 1.9% | 1.9% | 1.9% |
| Nattokinase | X | X | X | X | X | 0.5% | 0.5% |
| Keratinase | X | X | X | X | X | X | X |
| Proteinase | X | X | X | X | X | X | X |
| Lipase | X | X | X | 1.5% | 1.5% | 1.5% | 1.5% |
| Amylase | X | X | X | 1% | 1% | 1% | 1% |
| Cellulase | X | X | 4% | 2% | X | 2% | 2% |
| Temperature | 60 | 60 | 60 | 60 | 60 | 60 | 60 |
| Contact Time | 15 | 15 | 15 | 15 | 15 | 15 | 15 |
| Performance | Well at pH greater than 9 | Failed No degradation | Failed No degradation | Well at pH about 9 and above Significant reduction between pH 8 and 9 | Well at pH 10 and above | Good Some residual prion at pH9-9.5 | Well at pH slightly less than 9 and above |

NOTES TO TABLES:
Sonication is preferable to shake and shake preferable to soak.
A serine protease is required for full degradation of prions.
The addition of Celluclean to Solution 17 and 19 decreased the pH required for prion degradation by one unit from pH 10 to ≤pH 9.
Solution #12 is the detergent blend that was held constant in every formulation, which failed with pH range adjusted from neutral to 11. Detergent alone even when adjusted to pH 11 does not degrade prions.
Solution #13 is the detergent blend with the addition of Celluclean only without a serine protease or other enzymes and still failed at the tested pH range of neutral to pH 11. Celluclean alone when added to the detergent blend does not degrade prions

|  | 5A | 9 | 8 | 10 | A (a current formula) | B (a current formula) | 6A |
|---|---|---|---|---|---|---|---|
| Savinase | X | 1.9% | 1.9% | 1.9% | 1.9% | 1.9% | X |
| Alcalase | X | X | X | X | X | X | X |
| Nattokinase | X | 4% | 4% | X | X | X | 4% |
| Keratinase | 4% | 4% | X | 4% | X | X | X |
| Proteinase K | X | X | X | X | X | X | X |
| Lipase | X | 1.5% | 1.5% | 1.5% | 1.5% | 1.025% | X |
| Amylase | X | 1% | 1% | 1% | 1% | 0.625% | X |
| Cellulase | X | 4% | 4% | 4% | X | 0.035% | X |
| Temperature | 60 | 60 | 60 | 60 | 60 | 60 | 60 |
| Contact Time | 15 | 15 | 15 | 15 | 15 | 15 | 15 |
| Performance | Well at pH about 9.5 and above | Well at pH above 10 | Well* at pH 10 and above | Well* at pH 10 and above | Well** at pH 10 and above | Well** at pH 10 and above | Well at pH 10 Large reduction between pH 8 to 9 |

*lower pH worked well if sonication used
**at pH neutral to >9, failed by not degrading all the prions, however some degradation was observed at the lower pH in some cases Support for Potentially Disclaiming Aspects of Prior Art Existing formulations that are prior art to the present application are intended to be disclaimed from the formulation claims by the present inventor. In addition, the present inventor recognizes that some such formulations may be recommended for use under conditions which may approach those of some of the use claim limitations and to the extent that such exist, the use of such potential prior art formulation in such particular use conditions is also intended to be disclaimed from the use claims. To that end the following references are specifically incorporated by reference in their entireties for providing support for exclusionary statements that may be useful for the inventors to incorporate into the formulation and or use claims. It is intended that each limitation mentioned in each of the incorporated references may be independently used as an exclusionary or limiting limitation in either a positive or negative capacity, and any combination of a multiplicity of such limitations may be used in any such capacity. Finally, the limitations may be used as specific compounds, or genus of compounds, or particular method of use limitations for any set of components to which the use limitation applies. Given the foregoing statements of this paragraph, the following references are herein incorporated by reference in their entirety and may be explicitly reproduced herein in whole or in part if so required and be considered as if reproduced herein explicitly from the beginning; U.S. Pat. No. 4,511,400; U.S. Pat. No. 6,613,505; U.S. Pat. No. 7,303,907; U.S. Pat. No. 7,393,818; U.S. Pat. No. 8,034,766; U.S. Pat. No. 8,137,666; U.S. Pat. No. 8,431,526; US 2002/0192731; US 2004/0106188; US 2010/0260865; US 2011/0086414; WO 2002083082; WO 2008057293; and WO 2009052344 and the currently known marketed products known under the names Case Solutions, SuperNova Multi-Enzyme Cleaner (CSNC25, CSNC01), Pentaprep (CSA011), Pentazyme, NOVAPLUS and NOVAPLUS EXPRESS Multi-enzymatic cleaners and PentaWipes) marketed by Case Medical Inc); Cidex (sold by J&J), Empower (sold by Metrex), Prolystica and Klenzyme (sold by Steris), Ruhof, Getinge, EcoLab, and Certol.

I claim:

1. A method of treating a prion contaminated surface so that prion contamination which is be present on said surface is degraded so as to no longer he infectious, said surface selected from (a) medical devices used in the cutting into or being placed within a cavity within a human body, or in contact with (i) the blood stream, (ii) central nervous system tissue, (iii) brain tissue or eye tissue, (b) veterinary devices used in the cutting into or being placed within a cavity within an animal body, or in contact with (i) the blood stream, (ii) central nervous system tissue, (iii) brain tissue or eye tissue, and (c) implements used in the slaughter and/or processing of meat from an animal carcass for consumption as food,
said method consisting of
(A) contacting said surface with an enzymatic composition
(i) for an exposure time selected from time periods within the range of about 10 minutes to about 30 minutes;
(ii) said exposure time being at a temperature selected from temperatures within the range of 45° C to 65 ° C;
(iii) said contacting being a soak. operation optionally in the presence of one or both of sonication and agitation;

(B) optionally rinsing said substrate with water; and
(C) after said step (A) or after said step (B) when said step (B) is used, subjecting said surface to an additional disinfection or sterilization procedure, or combinations thereof wherein said additional disinfection or sterilization procedure is selected from the group consisting of an autoclave procedure, a steam sterilization procedure, or a gas plasma sterilization procedure or combinations thereof;
wherein said enzymatic composition consists of
(a) an amount selected from about 0..01% by weight to about 15% weight based on the complete composition of at least one prion digester enzyme selected from the group consisting of alcalase, savinase, and mixtures thereof,
(b) optionally one or more further enzymes selected from the group cons ting of one or more lipases; one or more amylases, one or more celluloses, one or more gluconases, and mixtures thereof, wherein said one of more gluconases are selected from the group consisting of endo-gluconases and exo-gluconases;
(c) surfactant portion consisting of one or more non-ionic surfactants, said one or more nonionic surfactants selected from the group consisting of polyethoxylated alcohols;
(d) sodium xylene sulfonate;
(e) optionally calcium chloride;
(f) about 1% to about 20% by weight of the composition of propylene glycol;
(g) a preservative;
(h) optionally one or more buffers selected from the group consisting of TRIS buffer, BICINE buffer, bicarbonate buffer and mixtures thereof, and optionally an appropriate pH adjuster; and
(i) reverse osmosis water or distilled water;
said enzymatic composition having a pH in the range of 9.1 to about 10.8;
which enzymatic composition may be used directly as is or in a dilution with reverse osmosis water or distilled water in an amount of 1 part by volume of the enzymatic composition with up to 128 parts by volume of said reverse osmosis water or distilled water.

2. The process of claim 1 wherein component (b) of the enzymatic composition is present and is at least one lipase, at least one amylase, and at least one cellulase.

3. The process of claim 1 wherein component (b) of the enzymatic composition is present and is at least one lipase, at least one amylase, and at least one gluconase, said at least one gluconase being selected from the group consisting of exo-gluconases and endo-gluconases.

4. The process of claim 1 wherein component (b) of the enzymatic composition is present and is at least one lipase, at least one amylase, at least one cellulase, and at least one gluconase, said at least one gluconase being selected from the group consisting of exo-gluconases and endo-gluconases.

5. The process of claim 1 wherein said calcium chloride is present.

6. The process of claim 1 wherein one or both of said buffer and said pH adjuster are present.

7. The process of claim 1 wherein the enzymatic composition consist;
(a) an amount selected from about 0.01% by weight to about 15% by weight based on the complete composition of at least one prion digester enzyme selected from the group consisting of alcalase, savinase, and mixtures thereof;

(b) one or more further enzymes selected from the group consisting of one or more lipases; one or more amylases, one or more cellulases, one or more gluconases, and mixtures thereof wherein said gluconases are selected from endo-gluconases and exo-gluconases;

(c) a surfactant portion consisting of one or more nonionic surfactants, said one or more nonionic surfactants selected from the group consisting of polyethoxylated alcohols;

(d) sodium xylene sulfonate;

(e) calcium chloride;

(f) about 1% to about 20% by weight of the composition of propylene glycol;

(g) a preservative;

(h) one or more buffers selected from the group consisting of TRIS buffer, BICINE buffer, bicarbonate buffer and mixtures thereof, and optionally an appropriate pH adjuster; and (i) reverse osmosis water or distilled water;

said composition having a pH in the range of 9.1 to about 10.8.

8. The process of claim 1 wherein the enzymatic composition consists of:

(a) an amount selected from about 0.01% by weight to about 15% by weight based on the complete composition of at least one prion digester enzyme selected from the group consisting of alcalase, savinase, and mixtures thereof;

(b) (i) one or more lipases;
(ii) one or more amylases;
(iii) one or more enzymes selected from the group consisting of cellulases, endo-gluconases; and exo-gluconases, and mixtures thereof;

(c) a surfactant portion consisting of one or more nonionic surfactants, said one or more nonionic surfactants selected from the group consisting of polyethoxylated alcohols;

(d) sodium xylene sulfonate;

(e) calcium chloride;

(f) about 1% to about 20% by weight of the composition of propylene glycol;

(g) a preservative;

(h) one or more buffers selected from the group consisting of TRIS buffer, BICINE buffer, bicarbonate buffer and mixtures thereof, and optionally an appropriate pH adjuster and (i) reverse osmosis water or distilled water;

said composition having a pH in the range of 9.1 to about 10.8.

9. The process of claim 8 wherein said component (b) (iii) is one or more cellulases.

10. The process of claim 8 wherein said component (b) (iii) is one or more of endo-gluconases or one or more of exo-gluconases, or mixtures thereof.

11. A method of treating a prion contaminated surface so that prion contamination which is be present on said surface is degraded so as to no longer be infectious, said surface selected from (a) medical devices used in the cutting into or being placed within a cavity within a human, body, or in contact with (i) the blood stream, (ii) central nervous system tissue, (iii) brain tissue or eye tissue, (h) veterinary devices used in the cutting into or being placed within a cavity within an animal body, or in contact with (i) the blood stream, (ii) central nervous system tissue, (iii) brain tissue or eye tissue, and (c) implements used in the slaughter and/or processing of meat from an animal carcass for consumption as food, said method consisting of (A) contacting said surface with an enzymatic composition
(i) for an exposure time selected from time periods within the range of about 10 minutes to about 30 minutes;
(ii) said exposure time being at a temperature selected from temperatures within the range of 45° C to 65° C;
(iii) said contacting being a soak operation optionally in the presence of one or both of sonication and agitation;

(B) subjecting said substrate to a non-enzymatic chemical cleaning;

(C) optionally rinsing said substrate with water;

after said step (B) or after said step (C) when said step (C) is used, subjecting said surface to an additional disinfection or sterilization procedure, or combinations thereof wherein said additional disinfection or sterilization procedure is selected from the group consisting of an autoclave procedure, a steam sterilization procedure, or a gas plasma sterilization procedure or combinations thereof;

wherein said enzymatic composition consists of
(a) an amount selected from about 0.01% by weight to about 15% by weight based on the complete composition of at least one prion digester enzyme selected from the group consisting of alcalase, savinase, and mixtures thereof;

(b) optionally one or more further enzymes selected from the group consisting of one or more lipases; one or more amylases, one or more cellulases, one or more gluconases, and mixtures thereof, wherein said. one of more gluconases are selected from the group consisting of endo-gluconases and exo-gluconases;

(c) a surfactant portion consisting of one or more non-ionic surfactants, said one or more nonionic surfactants selected from the group consisting of polyethoxylated alcohols;

(d) sodium xylene sulfonate;

(e) optionally calcium chloride;

(f) about 1% to about 20% by weight of the composition of propylene glycol;

(g) a preservative;

(h) optionally one or more buffers selected from the group consisting of TRIS buffer, BICINE buffer, bicarbonate buffer and mixtures thereof and optionally an appropriate pH adjuster; and (i) reverse osmosis water or distilled water;

said enzymatic composition having a pH in the range of 9.1 to about 10.8;

which enzymatic composition may be used directly as is or in a dilution with reverse osmosis water or distilled water in an amount of 1 part by volume of the enzymatic composition with up to 128 parts by volume of said reverse osmosis water or distilled water.

12. The method of claim 1 wherein said one or more further enzymes is present.

13. The method of claim 1 wherein said sonification is conducted while said surface is in contact with said composition.

14. The method of claim 1 wherein said rinsing step is conducted and carried out for at least 2 minutes.

* * * * *

UNITED STATES PATENT AND TRADEMARK OFFICE
CERTIFICATE OF CORRECTION

PATENT NO. : 10,669,513 B2
APPLICATION NO. : 15/720166
DATED : June 2, 2020
INVENTOR(S) : Frieze It is certified that error appears in the above-identified patent and that said Letters Patent is hereby corrected as shown below:

In the Claims

In Claim 1, at Column 17, Line 2, change the phrase "is be present" to "is present".

In Claim 1, at Column 17, Line 3, change the phrase "he infectious" to "be infectious".

In Claim 1, at Column 18, Line 1, change "substrate" to "surface".

In Claim 1, at Column 18, Line 11, change "0..01%" to "0.01%".

In Claim 1, at Column 18, Line 17, change "cons ting" to "consisting".

In Claim 1, at Column 18, Line 18, change "celluloses" to "cellulases".

In Claim 2, at Column 18, Line 1, replace "process" with "method".

In Claim 3, at Column 18, Line 1, replace "process" with "method".

In Claim 4, at Column 18, Line 1, replace "process" with "method".

In Claim 5, at Column 18, Line 1, replace "process" with "method".

In Claim 6, at Column 18, Line 1, replace "process" with "method".

In Claim 7, at Column 18, Line 1, replace "process" with "method".

In Claim 7, at Column 18, Line 2, change "consist" to "consists of".

In Claim 8, at Column 18, Line 1, replace "process" with "method".

Signed and Sealed this
Thirteenth Day of October, 2020

Andrei Iancu
*Director of the United States Patent and Trademark Office*

In Claim 9, at Column 18, Line 1, replace "process" with "method".

In Claim 10, at Column 18, Line 1, replace "process" with "method".

In Claim 11, at Column 19, Line 2, change the phrase "is be present" to "is present".

In Claim 11, at Column 20, Lines 13 and 15, change "substrate" to "surface".